United States Patent

Königer et al.

[11] Patent Number: 6,063,957
[45] Date of Patent: May 16, 2000

[54] PREPARATION OF ESTERS OF LOW RESIDUAL ACID CONTENT FROM α,β-ETHYLENICALLY UNSATURATED CARBOXYLIC ACIDS AND HYDROXYL-CONTAINING POLYMERS

[75] Inventors: Rainer Königer, Egelsbach; Wolfgang Reich, Maxdorf; Erich Beck, Ladenburg; Helmut Gruner, Schwarzheide, all of Germany

[73] Assignee: BASF Aktiengesellschaft, Ludwigshafen, Germany

[21] Appl. No.: 09/064,001

[22] Filed: Apr. 21, 1998

[30] Foreign Application Priority Data

Apr. 21, 1997 [DE] Germany .................. 197 16 686

[51] Int. Cl.$^7$ .................................................. C07C 67/48
[52] U.S. Cl. .................................................. 560/218
[58] Field of Search ................................. 560/218

[56] References Cited

U.S. PATENT DOCUMENTS 4,330,643  5/1982  Ogasawara et al. .
4,435,594  3/1984  Matsumura ............................ 560/218
5,246,993  9/1993  Scherzer et al. .

FOREIGN PATENT DOCUMENTS 0 126 341  11/1984  European Pat. Off. .
31 06 570   3/1982  Germany .
41 26 359   2/1993  Germany .

*Primary Examiner*—Paul J. Killos
*Attorney, Agent, or Firm*—Oblon, Spivak, McClelland, Maier & Neustadt, P.C.

[57] ABSTRACT

A process for preparing esters E of low residual acid content from α,β-monoethylenically unsaturated $C_3$–$C_6$ mono- and dicarboxylic acids S and hydroxyl-containing polycondensates P, where a) the acid S and the polycondensate P or the monomeric and/or oligomeric and/or polymeric components which form the polycondensate P, are reacted in the presence or absence of a solvent and/or of an esterification catalyst and/or of further additives, with removal of the water which forms, and b) the unreacted acid S is removed by distillation, comprises adding water for the distillative removal of the acid S in step b).

16 Claims, No Drawings

PREPARATION OF ESTERS OF LOW RESIDUAL ACID CONTENT FROM α, β-ETHYLENICALLY UNSATURATED CARBOXYLIC ACIDS AND HYDROXYL-CONTAINING POLYMERS

The present invention relates to a process for preparing esters of α,β-monoethylenically unsaturated mono- and dicarboxylic acids with hydroxyl-containing polyethers or polyesters (referred to below as polycondensates) in which the acid and the polymer are reacted to form an ester, with removal of the water which forms in the process, and the residual acid is separated off by distillation.

Esters of unsaturated carboxylic acids with hydroxyl-containing polycondensates have acquired great industrial importance and have found broad application in the form, for example, of the polyester and polyether acrylates and methacrylates. Their crosslinkability on exposure to light makes them particularly suitable for preparing radiation-curable coating compositions, such as paint formulations which can be cured rapidly by means of UV or electron beams. A reduction in the residual acid content is necessary, depending on the intended use of the esters, since the α,β-unsaturated mono- and/or dicarboxylic acids employed are not entirely unobjectionable from an allergological and toxicological standpoint, and may also lead to odor pollution. A low acid content is particularly desirable in the case of use inside as coatings, for example on wooden furniture, since otherwise the piece of furniture might become a source of irritating odors or skin irritants.

DE-A-33 16 593 describes a process for preparing esters of (meth)acrylic acid with hydroxyl-containing polyesters or polyethers, where esterification is carried out in the presence of an acidic esterification catalyst and at least one hydrocarbon which forms an azeotropic mixture with water and which is used as an entrainer for the water which is formed in the course of esterification and is distilled off azeotropically. Following esterification, the hydrocarbon is removed by distillation and the esterification catalyst is neutralized. Residual acrylic or methacrylic acid is removed by adding a polyepoxide compound in an amount equivalent to the acid number of the polyester acrylate or polyether acrylate. A disadvantage of this process is that, following the esterification with azeotropic removal of water and following the subsequent separation of the entrainer, the product still contains residual amounts of acrylic acid which have to be removed in an additional step by reaction with the epoxide. The prolonged reactor occupancy as a result of the additional reaction step, and the use of the relatively expensive epoxide, economically disadvantage this process. DE-A-38 43 854 describes a process for preparing (meth)acrylic esters of polyhydric alcohols by reacting the components in the presence of acidic esterification catalysts with addition of polymerization inhibitors, where the use of solvents and/or azeotropic entrainers is substantially avoided, the reaction space is flushed with an oxygen-containing gas stream, and the water of condensation formed in the course of the esterification is stripped off from the gas phase of the reaction space (air stripping). Following the reaction, the crude reaction product, which contains the acidic esterification catalyst, is subjected to dry neutralization by adding a neutralizing agent, for example an oxide and/or hydroxide of the alkali metals, of the alkaline earth metals and/or of aluminum. No reference is made to the residual acid content of the resulting esters. However, the products obtained are in many cases severely discolored and have to be treated at the end with decolorizers.

Ep-A-0 279 303 describes radiation-curable acrylates which are obtainable by a simultaneous reaction of polyhydric alkoxylated alcohols with a dibasic to tetrabasic $C_3$- to $C_6$-carboxylic acid or anhydrides thereof and with acrylic and/or methacrylic acid. This reaction takes place in the presence of an acidic esterification catalyst and at least one hydrocarbon, which forms an azeotropic mixture with water, and small amounts of a polymerization inhibitor, with the water which forms being removed azeotropically. Following distillative removal of the hydrocarbon and neutralization of the esterification catalyst, the excess carboxyl groups are reacted with an equivalent amount of an epoxide compound.

DE-A-28 38 691 describes radiation-curable acrylic polyesters and processes for their preparation, where a linear prepolymer having two terminal carboxyls or two terminal hydroxyls is reacted with at least one dihydroxyl compound or, respectively, with a dicarboxylic acid and the resulting product is subsequently esterified with acrylic acid. To remove the excess acrylic acid a solution of the polyester in an organic solvent, for example benzene, is washed several times with aqueous NaCl solutions and then the organic phase is dried over anhydrous sodium sulfate and filtered. A disadvantage of this process is the production of drying agents and washing waters polluted with organic compounds, which require complex workup or disposal. Moreover, repeated washing and then drying of the polyester acrylate-containing solutions leads to product losses.

DE-A-31 06 570 describes (meth)acryloyloxy-terminated polyesters which are prepared by reacting acrylic or methacrylic acid with a hydroxy-terminated polyester. The resulting reaction product can be purified by neutralization, washing with water, decolorization and filtration.

It is an object of the present invention to provide a simple process for preparing esters of α,β-monoethylenically unsaturated mono- and dicarboxylic acids and hydroxyl-containing polycondensates. The intention with this process, in particular, is to avoid the disadvantages of the hitherto customary processes for removing the residual acid by an additional reaction step, such as reaction with an epoxide or technically laborious stripping and washing techniques. The quality profile of the esters should be not substantially impaired, and in particular it should be possible to attain the same low residual acid contents that are possible in accordance with the prior art.

We have found that this object is achieved, surprisingly, if the unreacted acid is removed by distillation and at the same time water is added. In this case the residual acid contents achieved are essentially the same as those achieved with the processes customary to date.

The invention therefore provides a process for preparing esters E of low residual acid content from α,β-monoethylenically unsaturated $C_3$–$C_6$ mono- and dicarboxylic acids S and hydroxyl-containing polycondensates P (especially polyethers and polyesters), where a) the acid S and the polycondensate P, or the monomeric and/or oligomeric and/or polymeric components which form the polycondensate P, are reacted in the presence or absence of a solvent and/or of an esterification catalyst and/or of further additives, with removal of the water which forms, and b) the residual acid S is removed by distillation, which comprises adding water for the distillative removal of the acid S in step b).

Step a)

The esterification reaction between the α,β-monoethylenically unsaturated $C_3$–$C_6$ mono- and dicarboxylic acid S and the hydroxyl-containing polycondensates P takes place in accordance with generally known processes, it being possible for the water of reaction which has formed to be removed, for example, by means of water-removing agents, by extraction or azeotropically. The water of reaction which is formed is preferably removed azeotropically. In this case the reaction takes place in the presence of a solvent which forms an azeotropic mixture with water. Suitable solvents and entrainers are aliphatic and aromatic hydrocarbons, for example alkanes such as n-hexane and n-heptane, cycloalkanes such as cyclohexane and methylcyclohexane, aromatics such as benzene, toluene and xylene isomers, and petroleum fractions having boiling points of from 70 to 140° C. Particularly preferred entrainers are cyclohexane, methylcyclohexane and toluene. For the azeotropic removal of the water of reaction formed, the amount of solvent can be varied within wide ranges. Suitable apparatus for the azeotropic distillation with separation of the water of reaction and recycling of the solvent to the reaction vessel are known to the skilled worker. The solvent employed can be removed from the reaction mixture after esterification by customary methods, for example by distillation under atmospheric or reduced pressure. Advantageously, in the case of this distillation, some of the excess acid is already removed from the reaction mixture. The esterification is generally carried out at from about 60 to 140° C.

In the case of the novel esterification the degree of conversion is generally at least 85%, preferably from 90 to 95%. Esterification is generally carried out in the presence of a catalyst. Suitable catalysts are strong acids, for example sulfuric acid, anhydrous hydrogen chloride, sulfonic acids, for example toluene sulfonic acid, and acidic ion exchangers. In the novel process it is preferred to employ sulfuric acid and p-toluene sulfonic acid as catalyst. The amount of esterification catalyst in this case is generally within a range from about 0.1 to 5% by weight, based on the overall amount of components to be esterified.

To avoid premature polymerization the esterification in step a) takes place preferably in the presence of a polymerization inhibitor. Suitable polymerization inhibitors are the customary compounds used to prevent thermal polymerization, such as derivatives of hydroquinone, preferably hydroquinone monoalkyl ethers, for example hydroquinone monomethyl ether, substituted phenols, for example p-methoxyphenol, 2,5-di-t-butyl-p-cresol, 2,6-di-t-butylphenol, 2,6-di-t-butyl-4-methoxyphenol, 2-t-butyl-4-methoxyphenol, 3-t-butyl-4-methoxyphenol, 2,4,6-tri-t-butylphenol, etc., t-butylpyrocatechol, derivatives of N-nitrosamines, phenothiazine, phosphorous esters, such as triphenyl phosphite, diethyl phosphite, tridecyl phosphite, triisodecylphosphite, etc., and also hypophosphorous acid. They are generally employed in amounts from about 0.001 to 2.0% by weight, preferably from about 0.005 to 0.5% by weight, based on the overall amount of components to be esterified.

In another suitable embodiment the esters E can be prepared by reacting the acid S and the monomeric and/or oligomeric and/or polymeric components which form the polycondensate P, in the manner of a single-stage synthesis. Ep-A-0 279 303 describes a process for preparing radiation-curable acrylates by simultaneous reaction of all starting materials, and reference is hereby made to that document.

Step b)

In accordance with a general procedure, the residual acid S is removed in step b) of the novel process by distillation. The distillation can be carried out under atmospheric or reduced pressure. Distillation under reduced pressure is preferred, with just a slight vacuum being applied at the beginning, for example, and being increased, if desired, as the distillation progresses. Also possible, if desired, is distillation at constant pressure. In general the pressure in step b) is within a range from about 10 to 1000 mbar, preferably from 10 to 200 mbar and, in particular, from 15 to 50 mbar. Step b) is carried out at from about 80 to 130° C., preferably from about 90 to 120° C.

It has surprisingly now been found that the residual acid content of the esters E generally falls more quickly, and that generally even lower residual acid contents are obtained, if water is added to the reaction mixture in step b) before the distillation begins or in the course of the distillation. The water can be added in liquid or vapor form. If liquid water is added to the reaction batch, then the addition is made preferably below the liquid surface of the product obtained in step a), for example using a submerged pipe (dip tube). In this case the water can be added all at once or continuously, at the rate at which it is consumed, at the beginning of the distillation or not until there has been progress in the separation of the acid S and of any solvent likewise still present from step a). The addition of water is preferably not begun until any solvent from step a) still present has been almost entirely distilled off, or until the reaction batch has a residual acid content corresponding to an acid number of not more than 50 mg of KOH/g. The amount of water added can generally be varied within a wide range and is preferably from 0.005 g to 1.00 g per gram of components to be esterified from step a).

In a preferred embodiment of the novel process, a Lewis base, preferably a tertiary amine such as triethylamine, tripropylamine or tributylamine, or a quaternary ammonium compound such as tetraethylammonium bromide, tetrapropylammonium bromide or tetrabutylammonium bromide, is added to the reaction batch before adding the water and, if appropriate, after removing some of the acid in step b). Preferably, when a Lewis base is employed, the acidic esterification catalyst from step a) is substantially neutralized. A further advantage is that this addition generally avoids the discoloration of the resulting ester E.

To prepare the esters E in accordance with the invention the $\alpha,\beta$-monoethylenically unsaturated $C_3$–$C_6$ mono- and dicarboxylic acids S that are employed are selected from acrylic, methacrylic, maleic, fumaric and itaconic acid and mixtures thereof. Preferred acids S employed are acrylic acid, methacrylic acid and mixtures thereof.

The amount of acid S employed to prepare the esters E is generally from about 100 to 150 mol-% of carboxyl groups, based on free hydroxyl groups of the polycondensate P.

Suitable polycondensates P, which contain at least two free hydroxyls per molecule, are, for example, the customary polyesters with or without ether groups and polyethers with or without ester groups. Suitable hydroxyl-containing polyesters can be prepared, for example, in a customary manner by esterifying dibasic or polybasic carboxylic acids with dihydric or polyhydric alcohols. Processes for preparing polyesters are known to the skilled worker. The carboxylic acid component employed for the esterification in the preparation of hydroxyl-containing polyesters generally comprises dibasic to tetrabasic $C_3$- to $C_{36}$-carboxylic acids, their esters and anhydrides. Examples include succinic acid, succinic anhydride, glutaric acid, glutaric anhydride, adipic acid, sebacic acid, phthalic acid, phthalic anhydride, terephthalic acid, maleic acid, maleic anhydride, fumaric acid, citraconic acid, tetrahydrophthalic acid, tetrahydrophthalic anhydride, trimellitic acid, trimellitic anhydride, pyromellitic acid and pyromellitic anhydride. Examples of dihydric or polyhydric alcohols suitable as starting materials for preparing polyesters are dihydric to hexahydric alcohols, for example diols such as ethylene glycol, propylene glycol, 1,4-butanediol, 1,5-pentanediol, neopentyl glycol, 1,6-hexanediol, 2-methyl-1,5-pentanediol, 2-ethyl-1,4-butanediol, dimethylolcyclohexane, triols, such as glycerol, trimethylolethane, trimethylolpropane and trimethylolbutane, tetraols, such as pentaerythritol and ditrimethylolpropane and hexols, such as erythritol and sorbitol. Further suitable polyesterols are polycaprolactonediols and -triols.

further suitable hydroxyl-containing polycondensates P are the alkoxylates of the abovementioned dihydric or polyhydric alcohols. These include, for example, ethoxylated, propoxylated, and mixtures of ethoxylated and propoxylated, dihydric to hexahydric alcohols and polyesterols. The degree of alkoxylation is generally from 1 to 300, preferably from 2 to 150.

Other suitable polycondensates P are polyalkylene glycols and the polyaddition polymers of cyclic ethers, for example polytetrahydrofuran. Examples of polyalkylene glycols are polyethylene glycol, polypropylene glycol and polyepichlorohydrins.

Still further suitable polycondensates P are copolymers which contain in copolymerized form at least one of the abovementioned monomeric, oligomeric or polymeric components. These include, for example, polyesters of the abovementioned dibasic or polybasic carboxylic acids and alcohols with terminal carboxyls or hydroxyls, and polyetherols such as the abovementioned alkoxylates, polyalkylene glycols, and polymers of cyclic ethers.

Other suitable oligomeric or polymeric components are, for example, polyurethanes having terminal hydroxyls, polyesterpolyurethanes, which are obtainable from polyesters as diol component and diisocyanates or isocyanate-terminated prepolymers, and polyetherpolyurethanes, which are obtainable from polyethers as diol component and from the corresponding diisocyanates or isocyanate prepolymers.

Examples of other suitable oligomeric or polymeric components having free hydroxyls, such as bisphenol A diglycidyl ether, which have been cured, for example, with alcohols such as the abovementioned dihydric and polyhydric alcohols.

The esters E obtainable by the novel process from α,β-monoethylenically unsaturated carboxylic acids S and hydroxyl-containing polymers P have a residual acid content, determined as the acid number, of not more than 20 mg KOH/g, preferably not more than 15 mg of KOH/g.

For processing, the esters E prepared in accordance with the invention can be employed with further reactive diluents as customary for radiation curing. These include, for example, 4-t-butylcyclohexyl acrylate, phenoxyethyl acrylate, hexanediol diacrylate, tripropylene glycol diacrylate, trimethylolpropane diacrylate, and acrylates of alkoxylated diols and triols.

The novel esters E of low residual acid content are preferably suitable for preparing coating compositions. These compositions can judiciously be crosslinked either by means of electron beams or, with or without the addition of customary photoinitiators, by UV radiation and give films having good performance properties.

The invention is illustrated in more detail with reference to the following, nonlimiting examples.

EXAMPLES

The acid number is defined in mg of KOH/g of product and was determined in accordance with DIN 53402 or in accordance with the procedure of German Pharmacopeia 10, (1993) 3.4.1.

Example 1(Comparison)

38% by weight of triethoxylated trimethylolpropane, 37% by weight of acrylic acid and 24% by weight of methylcyclohexane are charged to a flask and 0.4% by weight of sulfuric acid is added. The mixture is stabilized with 0.21% by weight of hydroquinone monomethyl ether, 0.07% by weight of tert-butyl-p-cresol, 0.07% by weight of triphenyl phosphite, 0.07% by weight of hypophosphorous acid (50% strength in water) and 0.004% by weight of phenothiazine. Under reflux, 100% of the theoretically possible water volume is removed, a small proportion of the volume consisting of acrylic acid. Subsequently, a reduced-pressure gradient is carefully applied, in order to avoid foaming of the reaction mixture, and methylcyclohexane and acrylic acid are distilled off. In the course of this distillation the internal temperature rises to about 105° C. At an acid number of 46.5 mg of KOH/g, 0.1% by weight of tetrabutylammonium bromide solution (about 50% strength in water) is added. Distillation under reduced pressure is continued for a short time in order to remove the added water. A sample of this batch is taken and is heated under reduced pressure (33 mbar) to about 110° C,. and acrylic acid is distilled off. After 270 minutes the acid number has fallen to 15.1 mg of KOH/g.

Example 2

An 800 g sample of the batch from Example 1 is taken, after the addition of tetrabutylammonium bromide, and is heated under reduced pressure (35 mbar) to about 110° C. Water is slowly added dropwise to the resin by way of a submerged pipe. After 225 minutes and 170 ml of water introduced, the acid number has fallen to 3.1 mg of KOH/g.

Example 3

38% by weight of triethoxylated trimethylolpropane, 10% by weight of adipic acid, 25.5% by weight of acrylic acid and 25.5% by weight of methylcyclohexane are charged to a flask and 0.4% by weight of sulfuric acid is added. The mixture is stabilized with 0.22% by weight of hydroquinone monomethyl ether, 0.7% by weight of tert-butyl-p-kresol, 0.07% by weight of triphenyl phosphite, 0.07% by weight of hypophosphorous acid (50% strength in water) and 0.002% by weight of phenothiazine. Under reflux, 100% of the theoretically possible water volume is removed, some acrylic acid being separated off as well. Subsequently, a reduced-pressure gradient is applied, in order to avoid foaming of the reaction mixture, and methylcyclohexane and acrylic acid are distilled off. In the course of this distillation the internal temperature rises to about 105° C. At an acid number of about 40.7 mg of KOH/g, 0.1% by weight of tributylamine is added. 287 ml of water are added over a period of 90 minutes through a submerged pipe at 110° C. and 30 mbar. During this time the acid number falls to 11.3 mg of KOH/g.

As demonstrated by Examples 2 and 3 according to the invention, products with a lower acid number are obtained when water is added for the distillative separation of the acrylic acid. In this case, moreover, an advantage is that the acid number falls more quickly than it does without the addition of water.

we claim:

1. A process for preparing esters E of low residual acid content from α,β-monoethylenically unsaturated $C_3$–$C_6$ mono- and dicarboxylic acids S and hydroxyl-containing polycondensates P, where a) the acid S and the polycondensate P or the monomeric and/or oligomeric and/or polymeric components which form the polycondensate P, are reacted in the presence or absence of a solvent and/or of an esterification catalyst and/or of further additives, with removal of the water which forms, and b) the unreacted acid S is removed by distillation, which comprises adding water for the distillative removal of the acid S in step b).

2. A process as claimed in claim 1, wherein the water is added in liquid form in step b).

3. A process as claimed in claim 1, wherein step b) is carried out at from 80 to 130° C.

4. A process as claimed in claim 1, wherein the pressure in step b) is from 10 to 1000 mbar.

5. A process as claimed in claim 1, wherein some of the acid S and/or, if present, the solvent from step a) is removed by distillation before adding the water in step b).

6. A process as claimed in claim 1, wherein a Lewis base or a quaternary ammonium compound is added before adding the water and, if appropriate, after removing some of the acid S in step b).

7. A process as claimed in claim 1, wherein the reaction in step a) takes place in the presence of a solvent which forms an azeotropic mixture with water.

8. A process as claimed in claim 7, wherein the water formed in step a) is removed by azeotropic distillation in the course of esterification.

9. A process as claimed in claim 1, wherein the reaction in step a) takes place in the presence of an acidic esterification catalyst.

10. A process as claimed in claim 1, wherein the reaction in step a) takes place in the presence of a polymerization inhibitor as additive.

11. A process as claimed in claim 1, wherein the acid S is selected from acrylic, methacrylic, maleic, fumaric and itaconic acid and mixtures thereof.

12. A process as claimed in claim 11, wherein the acid S is selected from acrylic acid, methacrylic acid and mixtures thereof.

13. A process as claimed in claim 1, wherein the hydroxyl number of the polycondensate P is in the range from 50 to 900.

14. A process as claimed in claim 1, wherein the hydroxyl number of the polycondensate P is in the range from 300 to 650.

15. A process as claimed in claim 1, wherein the residual acid content of the ester E, determined as the acid number, is not more than 20 mg of KOH/g.

16. A process as claimed in claim 1, wherein the residual acid content of the ester E, determined as the acid number, is not more than 15 mg of KOH/g.

* * * * *